United States Patent [19]

Valenta et al.

[11] 4,186,737
[45] Feb. 5, 1980

[54] DRUG NEBULIZING SYSTEM FOR MEDICAL VENTILATORS OF THE VOLUME-LIMITED TYPE

[75] Inventors: James D. Valenta, Madison; Kenneth T. Heruth, Sun Prairie, both of Wis.

[73] Assignee: Airco, Inc., Montvale, N.J.

[21] Appl. No.: 850,326

[22] Filed: Nov. 10, 1977

[51] Int. Cl.² ............................................. A61M 16/00
[52] U.S. Cl. ............................ 128/203.28; 128/204.24
[58] Field of Search ............... 128/145.8, 145.5, 145.6, 128/188, 194

[56] References Cited

U.S. PATENT DOCUMENTS

| | | | |
|---|---|---|---|
| 3,530,856 | 9/1970 | Bird et al. | 128/145.6 |
| 3,537,449 | 11/1970 | Foxwell et al. | 128/145.5 |
| 3,863,630 | 2/1975 | Cavallo | 128/145.6 |
| 3,915,164 | 10/1975 | Bird | 128/145.8 |

FOREIGN PATENT DOCUMENTS

| | | |
|---|---|---|
| 1094370 | 12/1967 | United Kingdom . |
| 1212529 | 11/1970 | United Kingdom . |
| 1243765 | 8/1971 | United Kingdom . |
| 1377069 | 12/1974 | United Kingdom . |
| 1431081 | 4/1976 | United Kingdom . |
| 1444607 | 8/1976 | United Kingdom . |

*Primary Examiner*—Henry J. Recla
*Attorney, Agent, or Firm*—Roger M. Rathburn; Edmund W. Bopp; Larry R. Cassett

[57] ABSTRACT

An all-pneumatic medical ventilator of the volume-limited type is provided with a pneumatically driven drug nebulizer for injecting medication into the patient's breathing circuit in response to a cyclic pressure signal from the ventilator. The nebulizer is driven either directly or indirectly, according to the desired mode of use, from the pressurized oxygen source of the ventilator. In a preferred mode, a given portion of the tidal volume of gas is temporarily withdrawn from the breathing circuit during inhalation and subsequently forcibly returned by way of the nebulizer to the breathing circuit. This takes place during the same inhalation period so that nebulized medication is added to the patient's breathing circuit without changing either the predetermined oxygen concentration or tidal volume of the breathing gas.

7 Claims, 5 Drawing Figures

DRUG NEBULIZING SYSTEM FOR MEDICAL VENTILATORS OF THE VOLUME-LIMITED TYPE

BACKGROUND OF THE INVENTION

The use of volume-limited medical ventilators for providing a patient with breathing gas having a set oxygen concentration and tidal volume is shown for example, by U.S. Pat. No. 3,831,595, granted Aug. 27, 1974 to Valenta et al, and assigned to the same assignee as the present invention. In the use of such ventilators, the patient's treatment may sometimes call for the addition of a prescribed drug or medicine to the gas in the breathing circuit. Heretofore, it has been customary to administer the medicine or drug by means of an electrically operated auxiliary control system including a drug nebulizer connected to the breathing circuit and powered by a continuously running motor-driven compressor. However, electrical systems of such character when used with medical ventilators as described above, have significant disadvantages; for example, it is highly desirable from the safety standpoint that any electrical components or electrical connections which can be hazardous in the presence of oxygen, or oxygen-rich gases, be entirely eliminated from the equipment. Furthermore, the auxiliary electrical motor-compressor equipment requires a back-up source of electricity and is comparatively expensive.

In a known form of medical ventilator system for introducing medication by pneumatic nebulizing action, a combined humidifier and drug nebulizer unit is series-connected directly in the gas supply circuit leading to a main gas dispensing and measuring chamber for the breathing circuit. This arrangement is unsatisfactory as it creates problems such as contamination, due to condensation of drug-laden moisture in the measuring chamber during passage of the humidified gas therethrough to the breathing circuit. Accordingly, a sterilizing operation is required to clean the chamber, etc. after each patient-treatment.

In brief, drug nebulizing systems for medical ventilators such as described above, have been found unsatisfactory in practice for the reasons indicated, especially where an automatic, reliable, safe and clean system is desired for adding medication to the patient's breathing circuit.

The present invention therefore aims to provide an improved system and apparatus for overcoming disadvantages of the character described above, in the use of drug nebulizing means in volume-limited medical ventilator systems.

SUMMARY OF THE INVENTION

The present invention comprises essentially an all-pneumatic system for efficiently and safely injecting a medication into the breathing circuit of a volume-limited medical ventilator. In its simplest form, a nebulizer for administering the medication is connected directly to the breathing circuit immediately upstream of the patient's adapter or breathing tube. The nebulizer is driven by pressurized gas, the application of which is primarily controlled through an interface valve or equivalent, that in turn is triggered by or according to an "exhaust valve" pressure signal marking the start of inhalation. This pressure signal is produced by the ventilator according to the timing of the patient's inhale-exhale cycle. In this mode, the nebulizer is powered as long as the exhaust valve signal is applied to the interface valve, i.e. throughout the inhalation period; accordingly, the total volume of gas delivered to the patient depends on the total inhalation time.

In a more advanced form of the invention, a piston-controlled expansible-collapsible bellows is connected through one-way valves to the nebulizer and to the breathing circuit, respectively. The piston is operated by gas pressure according to the exhaust valve signal to collapse the bellows and expel gas therein, and has a spring-return for expanding the bellows. The expansion occurs during an exhalation period according to the exhaust valve signal, and during the expansion a unit-volume of gas is withdrawn from the oxygen control system of the ventilator. During the following inhalation, this volume of gas is expelled by piston action and returned to the breathing circuit by way of the drug nebulizer. In this form of the invention, the volume of breathing gas to the patient is increased by a known amount but its oxygen concentration is unchanged.

In a preferred form of the invention which also uses the spring-return, piston-bellows arrangement described above, the unit volume of gas is temporarily withdrawn directly from the normal breathing circuit during inhalation. In the same inhalation period, the piston under applied gas pressure compresses the bellows to expel and return the gas to the breathing circuit through the nebulizer. The desired sequence is controlled by a "one-shot" timing circuit that is triggered by an exhaust valve signal for controlling application of the spring and gas pressures to the bellows piston. In this preferred form, the total volume of gas transmitted to the patient is unchanged since the bellows sequence is within the limits of a single inhalation period; also the oxygen concentration of the reunited gas stream remains unchanged.

A principal object of the invention therefore is an improved system and apparatus for pneumatically injecting medication into the breathing circuit of a volume-limited medical ventilator that is efficient and reliable.

Another object of the invention is an improved system and apparatus of the character described above, having an auxiliary nebulizing system for injecting, during inhalation, the medication into the breathing circuit, that is pneumatically controlled for maintaining substantially constant the tidal volume and oxygen concentration of the patient's breathing gas.

Another object is an improved drug or medicine nebulizing system of the character described above, wherein the gas pressure driving the nebulizer is separately controlled by valve means responsive to a breathing-cycle signal generated by the ventilator.

Another and related object is an improved nebulizing system as described above wherein a unit volume of gas is temporarily withdrawn from the breathing circuit during inhalation and is forcibly returned to the circuit through a nebulizer for introducing the medication during the same inhalation period.

Other objects, features and advantages will appear from the following description with reference to the accompanying drawings.

DESCRIPTION OF PREFERRED EMBODIMENT OF INVENTION

Figure 1:
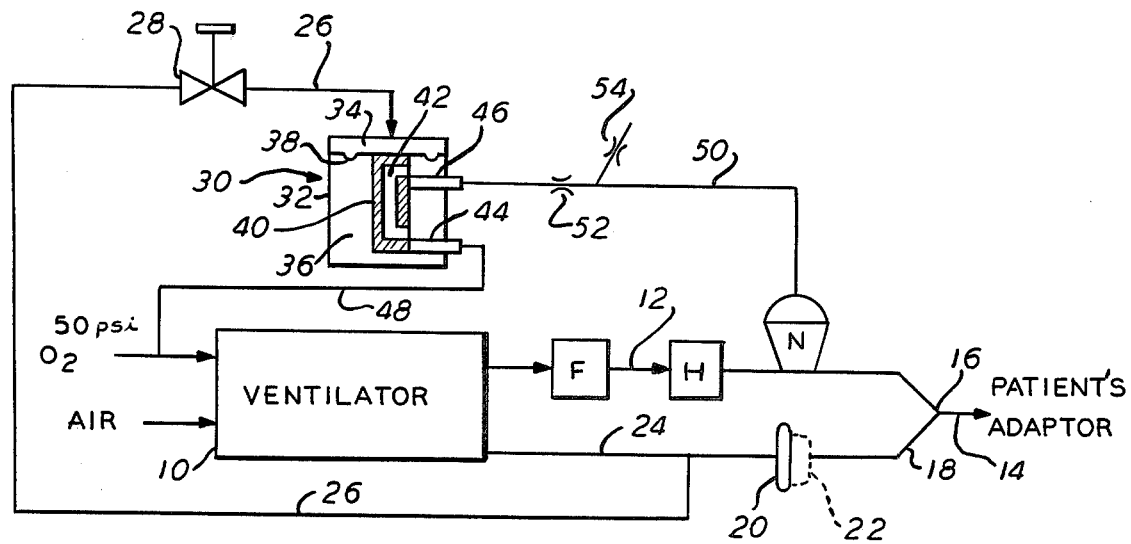
FIG. 1 is a schematic illustration of a drug nebulizing control system embodying the present invention as used with a medical ventilator of the volume-limited type.

Referring first to FIG. 1 which represents the simplest concept of the invention, the nebulizing system described below for adding medication to the patient's breathing gas is used in connection with a medical ventilator 10 that is of the all-pneumatic, volume-limited type such as disclosed in U.S. Pat. No. 3,831,595, above. A predetermined volume of gas for inhalation by the patient is delivered by this type ventilator through the breathing circuit 12, junction 16 and the patient's adapter line or breathing tube indicated at 14. This breathing gas also has a predetermined oxygen concentration depending on the ventilators setting. The ventilator system has, as indicated, a supply source of oxygen gas under pressure, such as 50 psi for example, and automatically adjusts the oxygen-air ratio according to a given setting.

The breathing circuit 12 has externally connected thereto immediately upstream of the patient's adapter 14 a drug or medicine nebulizer N having its outlet leading directly into the breathing circuit, as distinguished from a series-circuit connection. As shown, the nebulizer is connected to the breathing circuit downstream of conventional filter and humidifier apparatus F and H respectively, so that the medicated breathing gas goes directly to the patient.

The patient's adapter line 14 is also connected at junction 16 to a breath-exhaust line 18. This line is open-ended to atmosphere during exhalation, and is closed during inhalation by the diaphragm of an exhaust valve 20 of well-known mushroom type. The ventilator 10 produces a pressure signal during inhalation, that is transmitted through line 24 to the valve 20 so as to expand the diaphragm to the dotted-line position 22 and close the exhaust line 18. Thus, the exhaust line 18 is closed during inhalation to insure that all of the gas from the ventilator by way of the breathing circuit 12 is delivered to the patient's adaptor 14.

The diaphragm collapses to the solid-line position as the ventilator pressure signal is discontinued at the end of inhalation to allow the patient to freely exhale through the exhaust line 18. This ventilator pressure signal, herein called the "exhaust valve signal", controls either directly or indirectly, according to the mode of use of the invention, the operation of the nebulizer as will be hereinafter described. In FIG. 1, the exhaust valve signal from line 24 acts directly through line 26 and the "on-off" system valve 28 to control a fluidic-pneumatic interface valve 30 that, in turn, applies and shuts off pressurized gas to the nebulizer as the control signal is applied and removed, respectively. The interface valve is a commercially available device of well-known type, readily obtainable for example from Clippard Instrument Laboratories.

For purposes of illustration only, the interface valve 30 is schematically represented as a simple diaphragm arrangement for opening and closing a gas line interconnecting a source of gas pressure and the nebulizer. Briefly, the valve casing 32 is divided into chambers 34 and 36 by a flexible diaphragm-partition 38. The chamber 34 is connected to the incoming signal line 26. A valve member 40 in chamber 36 has a gas passage 42 open at its opposite ends, and is connected to the diaphragm 38 for movement therewith. When the diaphragm is depressed the valve is "ON" with the ends of the gas passage 42 in registry, respectively, with corresponding tubes 44 and 46 shown respectively, as extensions of the oxygen pressure source line 48, and a pressure-transmitting line 50 to the nebulizer N. For limiting the oxygen source pressure, which is given as 50 psi for example, pressure and flow control orifices 52 and 54 are suitably connected in and to the nebulizer pressure line 50 to reduce the pressure at the nebulizer to approximately 12 psi.

The nebulizer per se containing the drug or medicine can be of any suitable induction type, for example wherein a jet of pressurized gas is directed into a venturi passage or the like, thereby to induce flow of medicine or drug into the jet stream where it is nebulized and mixed with the gas as it leaves the nebulizer.

When there is no pressure signal in line 26, i.e. during exhalation, the interface valve 30 is in its "OFF" position indicated and no pressure is transmitted for driving the nebulizer. Conversely, during the inhalation period when the exhaust valve signal on line 26 is applied to the interface valve, pressurized gas is transmitted to the nebulizer. Thus, during inhalation, a pressure circuit is established for driving the nebulizer and introducing medication to the breathing circuit 12. In this mode, the nebulizer is powered throughout the length of the exhaust valve signal, i.e. the inhalation period, so that the gas volume (and oxygen concentration) received by the patient will depend on the length of this period. Accordingly, although the tidal volume of breathing gas and the oxygen concentration thereof are not precisely regulated according to FIG. 1, nevertheless this mode provides a practical and quite economical system for use with a volume-limited medical ventilator of the type described.

Figure 2:
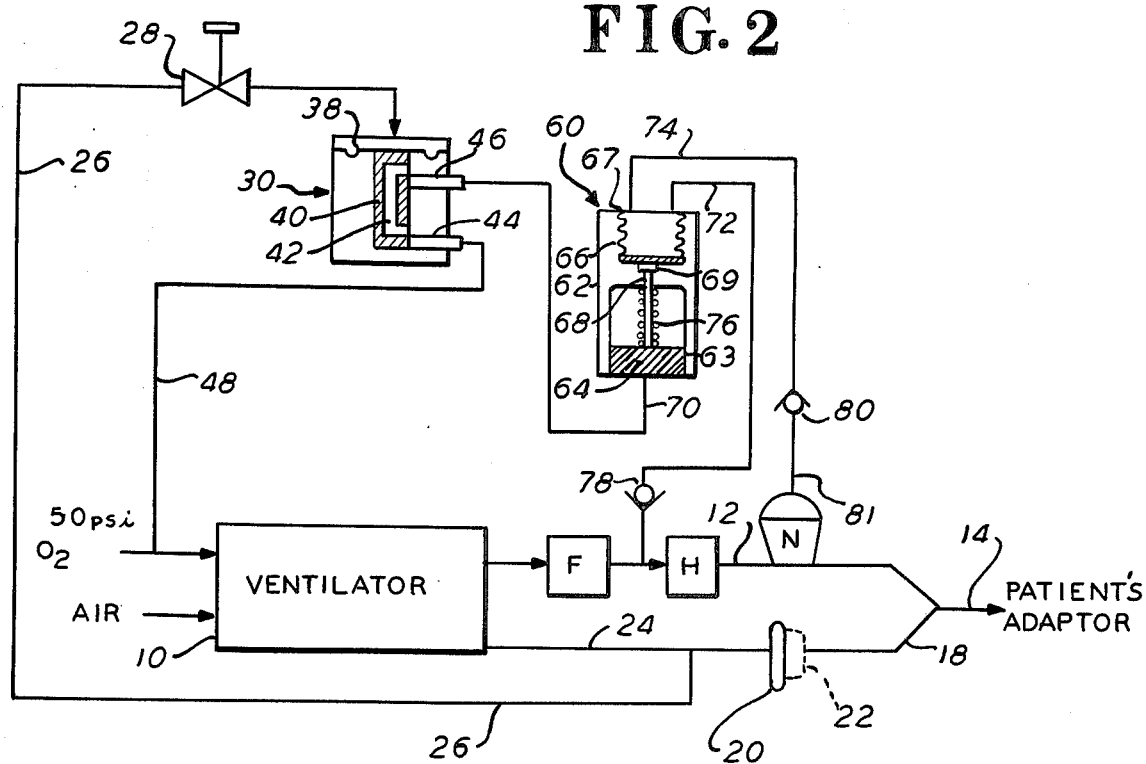
FIG. 2 shows another form of the invention in schematic form as in FIG. 1, wherein a portion of breathing gas is temporarily withdrawn from the system and subsequently returned through a drug nebulizer to the patient's breathing circuit.

FIG. 2 illustrates schematically a more advanced form of the invention wherein a given portion of breathing gas is temporarily withdrawn from the ventilator system by a piston-bellows device 60, and is subsequently returned under piston pressure to the breathing circuit 12 through the nebulizer N. In this form, the breathing circuit 12 and the exhaust-valve-signal control of the interface valve 30 are essentially as shown in FIG. 1; however, in FIG. 2 the piston-bellows device 60, rather than the nebulizer, is directly controlled by the interface valve 30. To this end, the device 60 comprises a supporting frame 62 in which are mounted a cylinder 63 with a reciprocal piston 64, and an expansible-collapsible bellows 66. One end of the bellows is secured to the frame at 67 and the other end is connected to the piston by rod 68. The working side of the piston is connected to a pressure line 70 from the interface valve 30 so that the oxygen source pressure can be available as shown, for driving the piston and compressing the bellows. The bellows interior communicates with a pair of conduits 72 and 74 for admitting and expelling gas to and from the bellows, respectively, as described below.

The piston, which has a pressure stroke and spring-return stroke, is suitably connected to spring structure 76 that is mounted in the cylinder 63 and stressed during the piston pressure stroke to store energy that subsequently is used for returning both the piston and bellows to their original positions shown, i.e. wherein the gas pressure in line 70 is cut off. For the purpose of regulating the volume of gas in the bellows 66 in the fully-expanded position shown, the piston-bellows connection 68 can be made linearly adjustable by a suitable coupling at 69.

The bellows conduits 72 and 74 are connected through one-way valves 78 and 80 respectively, to the breathing circuit 12 downstream of filter F, and to the nebulizer N, the arrangement shunting the humidifier H and being such that during spring-return of the piston 64 and expansion of the bellows 66, breathing gas is drawn from the ventilator system and through valve 78 into the bellows; during a gas pressure stroke of the piston, the bellows is forcibly collapsed to expel the withdrawn gas through both the valve 80 and nebulizer N and into the breathing circuit 12.

Accordingly, it will be seen that when the exhaust valve signal on line 26 is discontinued at the end of an inhalation period, the gas pressure on the piston 64 is cut off by the interface valve 30, thereby allowing the stressed spring 76 to return the piston to its starting point coincident with expansion of the bellows. This expansion draws residual breathing gas from the oxygen control system of the ventilator 10. The withdrawn breathing gas is retained in the bellows as long as the interface valve is "OFF", i.e. until a new inhalation period is started, at which time an exhaust valve signal appears on line 26 to switch gas pressure through the interface valve to the piston 64. As the piston is driven against the spring pressure to collapse the bellows, the portion of breathing gas temporarily stored in the bellows is expelled through the valve 80 and the nebulizer to inject medication into the breathing circuit.

In this arrangement the breathing gas is withdrawn only at the end of an inhalation period and is returned through the nebulizer at the beginning of the next inhalation period. Accordingly, the oxygen concentration of the breathing gas as set by the ventilator remains unchanged in this mode, the total gas volume however, being increased somewhat by a known portion added by the bellows.

Figure 3:
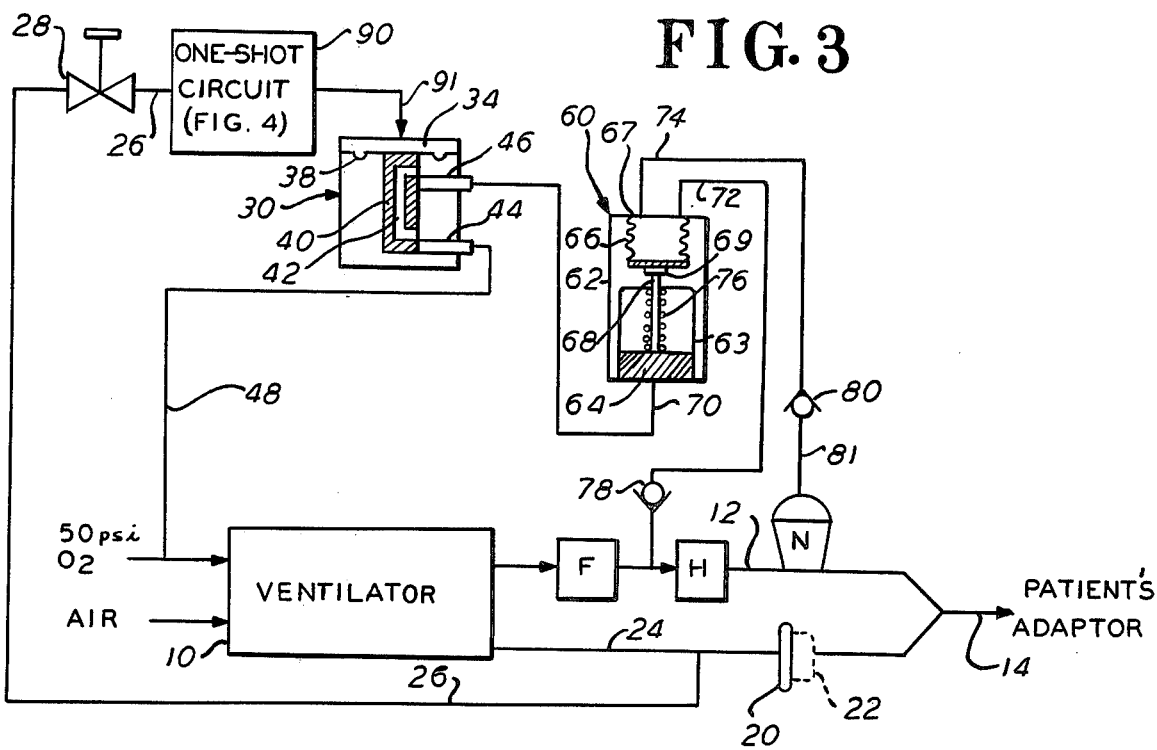
FIG. 3 is a schematic illustration of a preferred form of the invention that is generally similar to FIG. 2, with additional control means to schedule withdrawal of a portion of the breathing gas and return of the gas with medication to the breathing circuit during the same inhalation period.

In the preferred form of the invention, illustrated by FIG. 3, the breathing circuit, piston-bellows and nebulizer arrangements are essentially the same as in FIG. 2, with the same reference numbers indicating similar components; however, the exhaust valve signal from the line 26 is modified or programmed by a so-called "one-shot" circuit 90 for special control of the interface valve 30. The one-shot circuit is designed to modify the operation of the interface valve 30 so that the piston-bellows unit 60 is controlled to withdraw a portion of the normal tidal volume of breathing gas directly from the breathing circuit and to expel the gas during the same inhalation period, through the nebulizer N for return to the breathing circuit 12.

Figure 4:
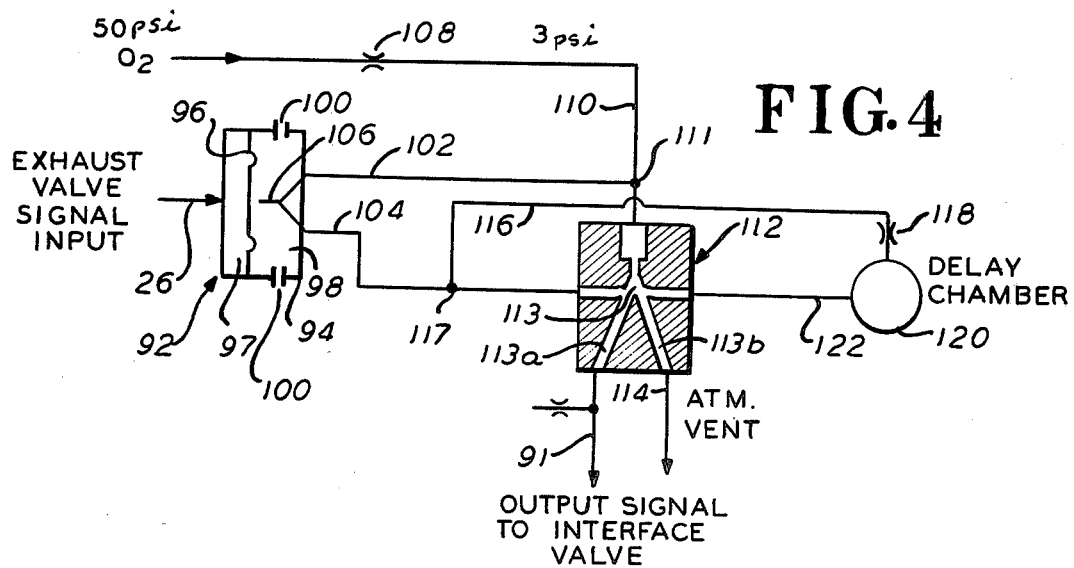
FIG. 4 is a diagrammatic illustration of the additional control means indicated in FIG. 3.

One form of pneumatic timing circuitry is diagrammatically illustrated by FIG. 4. This system uses a fluidic "one-shot" of known type. The exhaust-valve-signal line 26 is connected to a suitable type of diaphragm valve 92 comprising for examples, a housing 94 that is partitioned by a flexible diaphragm 96 to form two chambers, namely a signal-pressure chamber 97 and a valve chamber 98 having atmospheric vents 100. A pair of pneumatic lines 102 and 104 extend into the valve chamber 98 and are united by an open-end junction or connection 106. The open end of the junction forms the valve seat for the diaphragm 96, and is located opposite the central part of the diaphragm. Thus, when the diaphragm is flexed toward the right as shown, by signal pressure in the chamber 97, it closes the junction opening so that the lines 102 and 104 now form part of a continuous pneumatic circuit as described below.

The pressurized oxygen source for the system mentioned above, is also conveniently used in the operation of the pneumatic circuit 90, subject to suitable pressure reduction from 50 psi to about 3 psi by an orifice 108 or the like, in the pressure source line 110. This reduced pressure is connected through a known type of fluidic one-shot 112 having alternate outlets to either the input line 91 of the interface valve 30, FIG. 3, or to an atmospheric vent at 114 respectively. The main pressure line 110 leading to the one-shot 112 is also connected at junction 111 to the diaphragm-valve controlled line 102, which in turn is connected through line 104 to the one-shot. The line 104 is also connected through a line 116 with a flow reducing orifice 118, to a time-delay chamber 120 that also connects at its outlet through line 122 with the one-shot. The operation of the fluidic one-shot shown is based on the "Coanda effect" as described in "Computer Architecture" 2nd edition, C. A. Foster, pages 70–72.

A brief description of the fluidic one-shot circuitry shown by FIG. 4 follows. Assuming that the ventilator is in exhalation, there is a signal from the one-shot in outlet line 91 that actuates the interface valve 30 and holds the bellows 66 fully compressed. Now, if an inhalation begins, an exhaust valve pressure signal from the ventilator appears on the line 26 leading to the diaphragm valve 92. The valve diaphragm 96 is flexed by the pressure toward the right as shown, to close the vent opening of line junction 106, thereby completing a shunt circuit from the main pressure line 110 at junction 111 through the lines 102 and 104 to the stream control region 113 of the one-shot 112. The time-delay chamber 120 which is also connected to this circuit at junction 117, receives gas through the line 116 and flow-restricting orifice 118 at a predetermined rate that limits the rate of pressure buildup in the delay chamber 120; hence, significant gas flow from the chamber outlet line 122 to the stream transfer region 113 is delayed for a brief period. During this buildup of delay chamber pressure, gas flow from the line 104 into the control region predominates to bias the main flow from line 110 toward the right, i.e. into the atmospheric vent line 114. Accordingly, there is temporarily at the start of inhalation no pressure signal in the outlet line 91 leading to the interface valve 30. This valve therefore is now in the de-energized or "OFF" position as shown in FIG. 3, so that operating pressure for the bellows piston 64 is shut off, thereby allowing the bellows to expand and draw gas from the breathing circuit 12 as the stressed springs return the piston and bellows to their starting positions. Thus gas is withdrawn from the breathing circuit into the bellows during the first part of inhalation.

When the lateral opposing pressures of lines 104 and 122 are zero or substantially equal at the one-shot control region 113, the one-shot 112, due to its uni-stable design characteristic, tends to bias and lock the main flow from line 110 onto the left outlet passage 113a leading to line 91 and the interface valve 30.

After a brief interval at the first part of the inhalation period, the pressure buildup in the delay chamber 120 causes the pressure in the chamber outlet line 122 to increase to the point where it equals that in line 104. The resultant pressure is zero, so that the stream of gas from line 110 flips toward the left and locks onto the other outlet line 91 leading to the interface valve. The resulting pressure in line 91 causes operation of the interface valve 30 to complete the gas pressure circuit 48–50 to the bellows-piston unit. The piston, now driven by the pressurized gas, causes collapse of the bellows to expel the gas previously withdrawn from the breathing circuit, through the one-way valve 80, line 81 and nebulizer and into the breathing circuit. This operation, i.e. return of the withdrawn gas, now medicated, to the breathing circuit, takes place briefly during the early part of the inhalation period as the bellows piston, under full source pressure, drives the gas through the nebulizer N in a short-duration blast. The complete cycle of gas withdrawal, and return of medicated gas to the breathing circuit is therefore well within the time limits of a single inhalation period.

For the remainder of the inhalation period and throughout the following exhalation period, the bellows is held collapsed by the piston pressure so that it is in readiness at the beginning of the next inhalation period to withdraw gas from the breathing circuit.

Figure 5:
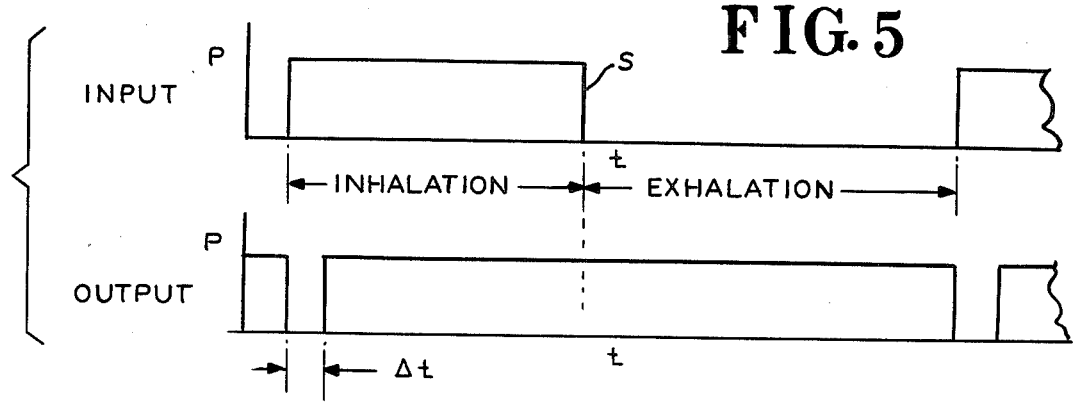
FIG. 5 is a pressure-time graph illustrating the operating characteristics of FIG. 4.

A sample operation in this mode is graphically illustrated by the P-t chart of FIG. 5, wherein "INPUT", i.e. the exhaust valve signal S at the diaphragm valve 92, is shown as applied only during the inhalation period indicated. The "OUTPUT" is represented on the same time scale. It is applied to the bellows piston except during a comparatively brief period, Δt, such as 0.3 sec., which is sufficient to allow the bellows piston to retract completely as described above. The pressure is then again applied, compressing the bellows. At the end of this stroke, the bellows is held compressed throughout inhalation. When the exhaust valve signal is cut off at the beginning of exhalation, the one-shot output signal at passage 113a and line 91 remains the same and the bellows remains compressed under piston pressure and is not released for expansion until the next exhaust valve signal.

The operation of the "one-shot" can be summarized as follows: during exhalation when there is no exhaust valve signal on line 26, the one-shot flow is normally along the left passage 113a and line 91, thereby biasing the interface valve to the "ON" position to apply pressure to the piston and hold the bellows collapsed.

When inhalation begins, a first stage is initiated wherein the diaphragm valve 92 in response to the exhaust valve signal, causes the one-shot pressure flow to swing to the right-hand passage 113b and atmospheric vent 114. This temporarily removes the signal on the interface valve 30 which cuts "OFF" and takes gas pressure off the piston 64. The bellows then expands under spring force to withdraw gas from the breathing circuit. The second stage occurs at the end of the gas withdrawal time interval Δt, when the pressure in the one-shot time delay chamber 120 has built up to stabilize the pressures in lines 104 and 122, thereby causing the one-shot pressure flow to revert to the left passage 113a and the interface valve line 91. Thus, the valve 30 is again actuated, causing a piston stroke and ejection of the withdrawn gas from the bellows during the same inhalation period as shown in FIG. 5.

Having set forth the invention in what is considered to be the best embodiment thereof, it will be understood that changes may be made in the system and apparatus as above set forth without departing from the spirit of the invention or exceeding the scope thereof as defined in the following claims.

We claim:

1. A drug nebulizer control system for adding medication to a patient's breathing gas from a medical ventilator of the volume limited type having an inhalation phase where gas having a predetermined oxygen concentration is delivered to the patient and an exhalation phase, said system comprising:
    (a) a patient gas breathing line adapted to receive breathing gas from the ventilator and deliver said gas to the patient during the inhalation phase,
    (b) drug nebulizing means connected to said breathing line and adapted to be powered by a pressurized gas to cause injection of nebulized medication into said breathing line,
    (c) means to withdraw a predetermined volume of gas of predetermined oxygen concentration supplied from said ventilator during its inhalation phase, and
    (d) means to pressurize said withdrawn predetermined volume of gas during the same inhalation phase and apply said pressurized gas to said nebulizing means for powering said nebulizing means to inject the nebulized medication into said breathing line.

2. A control system as defined in claim 1 wherein said means to withdraw a predetermined volume of gas comprises an expansible-collapsible chamber, said chamber being operatively connected to said nebulizing means and adapted to expand to withdraw said gas and said means to pressurize said withdrawn gas collapses said same expansible-collapsible chamber, whereby said chamber collapses to pressurize said gas and apply said gas to said drug nebulizing means.

3. A control system as defined in claim 2 wherein said expansible-collapsible chamber comprises a bellows that is operably connected to a piston, and said means to pressurize includes control means provided to move said piston to collapse and expand said bellows.

4. A control system as defined in claim 2 wherein said means to pressurize includes control means provided to expand said expansible-collapsible chamber said inhalation phase of the ventilator to withdraw said gas and to collapse said expansible-collapsible chamber to pressurize said withdrawn gas and apply said gas to said nebulizing means during the same inhalation phase of the ventilator.

5. A control system as defined in claim 3 wherein said piston is pressure actuated to collapse said bellows and spring bias means is provided to move said piston to expand said bellows.

6. A control system as defined in claim 2 wherein said means to pressurize includes control means provided to both expand and collapse said expansible-collapsible chamber during the same inhalation phase of the ventilator.

7. A control system as defined in claim 6 wherein said control means comprises means to expand said expansible-collapsible chamber during the first part of an inhalation phase of the ventilator, means to hold said chamber in its expanded state for a period of time, and means to collapse said expansible-collapsible chamber during the same inhalation phase.

* * * * *